US012462663B2

(12) United States Patent
Kanukurthy et al.

(10) Patent No.: US 12,462,663 B2
(45) **Date of Patent: *Nov. 4, 2025**

(54) SELF-CHECK FOR PERSONAL PROTECTIVE EQUIPMENT

(71) Applicant: 3M INNOVATIVE PROPERTIES COMPANY, St. Paul, MN (US)

(72) Inventors: Kiran S. Kanukurthy, Cottage Grove, MN (US); Steven T. Awiszus, Woodbury, MN (US); Eric C. Lobner, Woodbury, MN (US); Michael G. Wurm, Waukesha, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,123

(22) Filed: Jun. 4, 2024

(65) Prior Publication Data

US 2024/0321081 A1 Sep. 26, 2024

Related U.S. Application Data

(63) Continuation of application No. 18/321,493, filed on May 22, 2023, now Pat. No. 12,033,488, which is a
(Continued)

(51) Int. Cl.
*G08B 21/18* (2006.01)
*G08B 21/12* (2006.01)
(Continued)

(52) U.S. Cl.
CPC ........... *G08B 21/182* (2013.01); *G08B 21/12* (2013.01); *G08B 25/016* (2013.01); *G08B 25/10* (2013.01); *G16H 40/63* (2018.01); *G16H 40/40* (2018.01)

(58) Field of Classification Search
CPC .... G08B 21/182; G08B 21/12; G08B 25/016; G08B 25/10; G08B 19/00; G16H 40/63;
(Continued)

(56) References Cited

U.S. PATENT DOCUMENTS 7,464,001 B1 12/2008 Adams
9,974,969 B2 * 5/2018 Elghazzawi ........... G16H 40/40
(Continued)

FOREIGN PATENT DOCUMENTS

EP 2362332 A1 8/2011
WO 2016089708 A1 6/2016

OTHER PUBLICATIONS

International Search Report for PCT International Application No. PCT/US2017/056184, mailed on Jan. 5, 2018, 4 pages.

*Primary Examiner* — Brandon J Miller
(74) *Attorney, Agent, or Firm* — Christopher D. Karlen; Steven A. Bern; Sriram Srinivasan

(57) ABSTRACT

In some examples, a system includes a plurality of articles of personal protected equipment (PPE) that are each assigned to a particular worker. The system may also include a data hub that detects an input that initiates a broadcast of diagnostic self-check messages; identifies, in response to the input, each article of PPE of the plurality of articles of PPE; broadcasts, based on identifying each article of PPE, the diagnostic self-check messages to the respective articles of PPE, wherein each article of PPE receives its respective self-check message at its communication component; in response to receiving a set of diagnostic acknowledgement messages from one or more of the plurality of articles of PPE that have performed a diagnostic self-check, determines whether the set of diagnostic acknowledge messages satisfy
(Continued)

one or more self-check criteria; and performs one or more operations based on whether the self-check criteria are satisfied.

15 Claims, 5 Drawing Sheets

Related U.S. Application Data continuation of application No. 17/446,622, filed on Sep. 1, 2021, now Pat. No. 11,694,536, which is a continuation of application No. 16/946,692, filed on Jul. 1, 2020, now Pat. No. 11,127,277, which is a continuation of application No. 16/714,870, filed on Dec. 16, 2019, now Pat. No. 10,741,052, which is a continuation of application No. 16/340,714, filed as application No. PCT/US2017/056184 on Oct. 11, 2017, now Pat. No. 10,515,532.

(60) Provisional application No. 62/408,353, filed on Oct. 14, 2016.

(51) Int. Cl.

| | |
|---|---|
| ***G08B 25/01*** | (2006.01) |
| ***G08B 25/10*** | (2006.01) |
| ***G16H 40/40*** | (2018.01) |
| ***G16H 40/63*** | (2018.01) |

(58) Field of Classification Search

CPC ...... G16H 40/40; G16H 40/67; G06Q 50/265; A42B 3/30

See application file for complete search history.

(56) References Cited

U.S. PATENT DOCUMENTS

| | | | | |
|---|---|---|---|---|
| 9,998,804 | B2 | 6/2018 | Awiszus et al. | |
| 10,055,971 | B2 | 8/2018 | M R et al. | |
| 10,108,783 | B2 | 10/2018 | Horseman | |
| 10,515,532 | B2 * | 12/2019 | Kanukurthy | G08B 25/10 |
| 10,741,052 | B2 * | 8/2020 | Kanukurthy | G16H 40/63 |
| 11,127,277 | B2 * | 9/2021 | Kanukurthy | G08B 25/016 |
| 11,694,536 | B2 * | 7/2023 | Kanukurthy | G08B 25/016 455/404.1 |
| 12,033,488 | B2 * | 7/2024 | Kanukurthy | G16H 40/63 |
| 2008/0001735 | A1 | 1/2008 | Tran | |
| 2011/0006894 | A1 | 1/2011 | Witwer et al. | |
| 2012/0081214 | A1 | 4/2012 | Alan | |
| 2014/0032236 | A1 | 1/2014 | Williams et al. | |
| 2016/0067531 | A1 * | 3/2016 | Pariseau | A62B 9/006 128/204.18 |
| 2017/0372216 | A1 | 12/2017 | Awiszus et al. | |
| 2018/0107169 | A1 | 4/2018 | Hu et al. | |
| 2018/0270549 | A1 | 9/2018 | Awiszus et al. | |
| 2019/0007540 | A1 * | 1/2019 | Shaik | H04M 1/6066 |
| 2019/0175961 | A1 | 6/2019 | Awiszus et al. | |

* cited by examiner

SELF-CHECK FOR PERSONAL PROTECTIVE EQUIPMENT

CROSS REFERENCE TO RELATED APPLICATIONS

This application is a continuation of U.S. application Ser. No. 18/321,493, filed May 22, 2023, now allowed, which is a continuation of U.S. application Ser. No. 17/446,622, filed Sep. 1, 2021, issued as U.S. Pat. No. 11,694,536, which is a continuation of U.S. application Ser. No. 16/946,692, filed Jul. 1, 2020, issued as U.S. Pat. No. 11,127,277, which is a continuation of U.S. application Ser. No. 16/714,870, filed Dec. 16, 2019, issued as U.S. Pat. No. 10,741,052, which is a continuation of U.S. application Ser. No. 16/340,714, filed Apr. 10, 2019, issued as U.S. Pat. No. 10,515,532, which is a national stage filing under 35 U.S.C. 371 of PCT/US2017/056184, filed Oct. 11, 2017, which claims priority to U.S. Provisional Application No. 62/408,353, filed Oct. 14, 2016, the disclosure of which is incorporated by reference in its/their entirety herein the disclosure of which is incorporated by reference in their entirety herein.

TECHNICAL FIELD

This disclosure relates to safety equipment and, in particular, using safety equipment in a work environments.

BACKGROUND

Maintaining the safety and health of workers is a major concern across many industries. Various rules and regulations have been developed to aid in addressing this concern. Such rules provide sets of requirements to ensure proper administration of personnel health and safety procedures. To help in maintaining worker safety and health, some individuals may be required to don, wear, carry, or otherwise use a personal protective equipment (PPE) article, if the individuals enter or remain in work environments that have hazardous or potentially hazardous conditions.

Known types of PPE articles include, without limitation, respiratory protection equipment (RPE), e.g., for normal condition use or emergency response; protective eyewear, such as visors, goggles, filters or shields; protective headwear, such as hard hats, hoods or helmets; hearing protection devices; protective shoes; protective gloves; other protective clothing, such as coveralls and aprons; protective articles, such as sensors, safety tools, detectors, global positioning devices, mining cap lamps and any other suitable gear. In some instances, a worker may operate in a work environment with multiple different articles of personal protective equipment.

SUMMARY

In general, this disclosure describes techniques and components for performing a diagnostic self-check of PPE worn by or assigned to a worker. For instance, a worker may be equipped with multiple different articles of PPE, each of which includes a communication component and hardware that generates operating condition states for one for one or more operating conditions. In some examples, the worker may be equipped with a data hub that is communicatively coupled to the multiple different articles of PPE assigned to the worker. In response to receiving an input, the data hub may initiate a self-check procedure in which self-check messages are broadcasted to each article of PPE that is communicatively coupled to the data hub. Each article of PPE may update and/or select its operating condition states and send a diagnostic acknowledgement message to the data hub that indicates the operating condition states and/or whether a self-check performed at the article of PPE indicates that the article of PPE is operating correctly. The data hub may receive the diagnostic acknowledgement messages and perform one or more operations based on whether each article of PPE is operating correctly. In this way, techniques and components of this disclosure may enable a worker to determine if the set of PPE is operating correctly without further technical dissection or evaluation of the PPE, which may not be possible in some environments. Furthermore, whether each article of PPE is operating correctly may be further processed by a remote computing device, such as a PPE management system to provide for alerts and analytics analysis of the PPE.

In some examples, a system includes: a plurality of articles of personal protected equipment (PPE) that are each assigned to a particular worker, wherein each article of PPE of the plurality of articles of PPE includes a respective communication component; a data hub assigned to the particular worker comprising one or more computer processors, and a memory comprising instructions that when executed by the one or more computer processors cause the one or more computer processors to: detect an input that initiates a broadcast of diagnostic self-check messages; identify, in response to the input, each article of PPE of the plurality of articles of PPE; broadcast, based on identifying each article of PPE, the diagnostic self-check messages to the respective articles of PPE, wherein each article of PPE receives its respective self-check message at its communication component; in response to receiving a set of diagnostic acknowledgement messages from one or more of the plurality of articles of PPE that have performed a diagnostic self-check, determine whether the set of diagnostic acknowledge messages satisfy one or more self-check criteria; and perform one or more operations based at least in part on whether the one or more self-check criteria are satisfied.

In some examples, a computing device includes: one or more computer processors; and a memory comprising instructions that when executed by the one or more computer processors cause the one or more computer processors to: detect an input that initiates a broadcast of diagnostic self-check messages; identify, in response to the input, each article of PPE of a plurality of articles of PPE that are communicatively coupled to the computing device; broadcast, based on identifying each article of PPE, the diagnostic self-check messages to the respective articles of PPE, wherein each article of PPE receives its respective self-check message at its communication component; in response to receiving a set of diagnostic acknowledgement messages from one or more of the plurality of articles of PPE that have performed a diagnostic self-check, determine whether the set of diagnostic acknowledge messages satisfy one or more self-check criteria; and perform one or more operations based at least in part on whether the one or more self-check criteria are satisfied.

In some examples, a method includes: detecting, by a computing device, an input that initiates a broadcast of diagnostic self-check messages; identifying in response to the input, each article of PPE of a plurality of articles of PPE that are communicatively coupled to the computing device; broadcasting, based on identifying each article of PPE, the diagnostic self-check messages to the respective articles of PPE, wherein each article of PPE receives its respective self-check message at its communication component; in response to receiving a set of diagnostic acknowledgement messages from one or more of the plurality of articles of PPE that have performed a diagnostic self-check, determining whether the set of diagnostic acknowledge messages satisfy one or more self-check criteria; and performing one or more operations based at least in part on whether the one or more self-check criteria are satisfied.

The details of one or more examples are set forth in the accompanying drawings and the description below. Other features, objects, and advantages of the disclosure will be apparent from the description and drawings, and from the claims.

DETAILED DESCRIPTION

Figure 1:
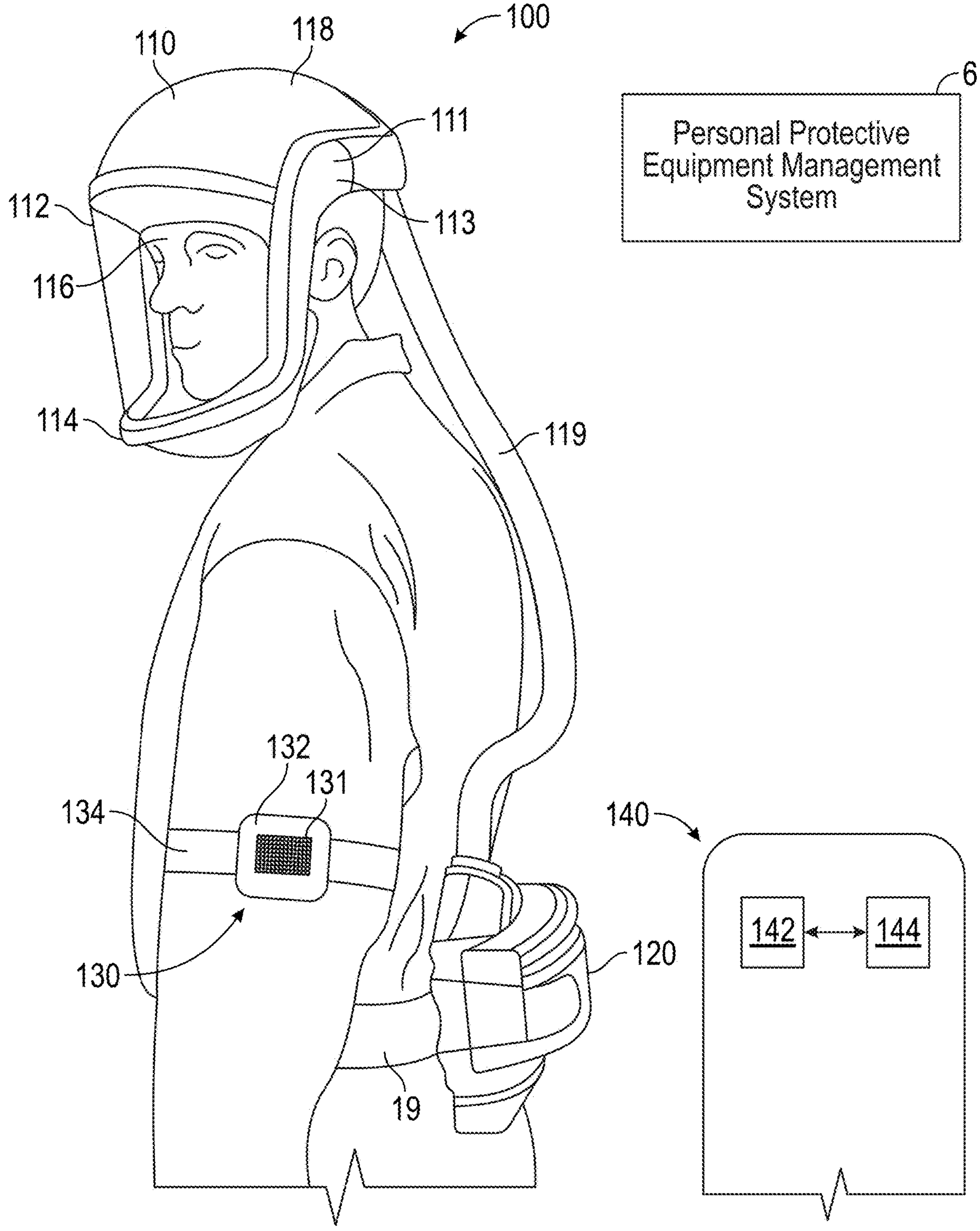
FIG. 1 is a conceptual diagram of a data hub configurable to perform a PPE self-check procedure in accordance with one or more techniques of this disclosure.

FIG. 1 is a conceptual diagram of a data hub configurable to perform a PPE self-check procedure in accordance with one or more techniques of this disclosure. As shown in FIG. 1, a worker is wearing supplied air respirator system 100. System 100 includes head top 110, clean air supply source 120, and data hub 130. Head top 110 is connected to clean air supply source 120 by hose 119. Clean air supply source 120 can be any type of air supply source, such as a blower assembly for a powered air purifying respirator (PAPR), an air tank for a self-contained breathing apparatus (SCBA) or any other device that provides air to head top 110. In FIG. 1, clean air supply source 120 is a blower assembly for a PAPR. A PAPR is commonly used by individuals working in areas where there is known to be, or there is a potential of there being dusts, fumes or gases that are potentially harmful or hazardous to health. A PAPR typically includes blower assembly, including a fan driven by an electric motor for delivering a forced flow of air to the respirator user. The air is passed from the PAPR blower assembly through hose 119 to the interior of head top 110.

Head top 110 includes a visor 112 that is sized to fit over at least a user's nose and mouth. Visor 112 includes lens 116 which is secured to helmet 118 by the frame assembly 114. Head top also includes a position sensor 111 that senses the position of visor 112 relative to helmet 118 to determine if the visor is in an open position or in a closed position. In some instances, position sensor 111 may detect whether visor 112 is partially open, and if so, what measure (e.g., percent or degree) it is open. As an example, the position sensor 110 may be a gyroscope that computes angular yaw, pitch, and/or roll (in degrees or radians) of the visor 112 relative to the helmet 118. In another example, the position sensor 110 may be a magnet. A percent may be estimated respecting how open a visor 112 is in relation to the helmet 118 by determining the magnetic field strength or flux perceived by the position sensor 110. "Partially open" visor information can be used to denote that the user may be receiving eye and face protection for hazards while still receiving a reasonable amount of respiratory protection. This "partially open" visor state, if kept to short durations, can assist the user in face to face communications with other workers. Position sensor 111 can be a variety of types of sensors, for example, an accelerometer, gyro, magnet, switch, potentiometer, digital positioning sensor or air pressure sensor. Position sensor 111 can also be a combination of any of the sensors listed above, or any other types of sensors that can be used to detected the position of the visor 112 relative to the helmet 118.

Head top 110 may include other types of sensors. For example, head top 110 may include temperature sensor 113 that detects the ambient temperature in the interior of head top 110. Head top 110 may include other sensors such as an infrared head detection sensor positioned near the suspension of head top 110 to detect the presence of a head in head top 110, or in other words, to detect whether head top 110 is being worn at any given point in time. Head top 110 may also include other electronic components, such as a communication module, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module in head top 110 can electronically interface with sensors, such as position sensor 111 or temperature sensor 113, such that it can transmit information from position sensor 111 or temperature sensor 113 to other electronic devices, including data hub 130.

Data hub 130 may be portable such that it can be carried or worn by a user. Data hub 130 can also be personal, such that it is used by an individual and communicates with personal protective equipment (PPE) assigned to that individual. In FIG. 1, data hub 130 is secured to a user using a strap 134. However, data hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Environmental beacon 140 includes at least environmental sensor 142 which detects the presence of a hazard and communication module 144. Environmental sensor 142 may detect a variety of types of information about the area surrounding environmental beacon 140. For example, environmental sensor 142 may be a thermometer detecting temperature, a barometer detecting pressure, an accelerometer detecting movement or change in position, an air contaminant sensor for detecting potential harmful gases like carbon monoxide, or for detecting air-born contaminants or particulates such as smoke, soot, dust, mold, pesticides, solvents (e.g., isocyanates, ammonia, bleach, etc.), and volatile organic compounds (e.g., acetone, glycol ethers, benzene, methylene chloride, etc.). Environmental sensor 142 may detect, for example any common gasses detected by a four gas sensor, including: CO, O2, HS and Low Exposure Limit. In some instances, environmental sensor 142 may determine the presence of a hazard when a contaminant level exceeds a designated hazard threshold. In some instances, the designated hazard threshold is configurable by the user or operator of the system. In some instances, the designated hazard threshold is stored on at least one of the environmental sensor and the personal data hub. In some instances, the designated hazard threshold is stored at personal protective equipment management system (PPEMS) 6 (further described in FIGS. 3-4) and can be sent to data hub 130 or environmental beacon 140 and stored locally on data hub 130 or environmental beacon 140.

Environmental beacon 140 and communication module 144 are electronically connected to environmental sensor 142 to receive information from environmental sensor 142. Communication module 144 may include a variety of communication capabilities, such as: RFID, Bluetooth, including any generations of Bluetooth technology, and WiFi communication capabilities. Data hub 130 can also include any type of wireless communication capabilities, such as radio frequency or Zigbee communication.

In some instances, environmental beacon 140 may store hazard information based on the location of environmental beacon 140. For example, if environmental beacon 140 is in an environment known to have physical hazards, such as the potential of flying objects, environmental beacon 140 may store such information and communicate the presence of a hazard based on the location of environmental beacon 140. In other instances, the signal indicating the presence of a hazard may be generated by environmental beacon 140 based on detection of a hazard by environmental sensor 142.

The system may also have an exposure threshold. An exposure threshold can be stored on any combination of PPEMS 6, data hub 130, environmental beacon 140, and head top 110. A designated exposure threshold is the time threshold during which a visor 112 can be in the open position before an alert is generated. In other words, if the visor is in the open position for a period of time exceeding a designated exposure threshold, an alert may be generated. The designated exposure threshold may be configurable by a user or operator of the system. The designated exposure threshold may depend on personal factors related to the individual's health, age, or other demographic information, on the type of environment the user is in, and on the danger of the exposure to the hazard.

An alert can be generated in a variety of scenarios and in a variety of ways. For example, the alert may be generated by the data hub 130 based on information received from head top 110 and environmental sensor 140. An alert may be in the form of an electronic signal transmitted to PPEMS 6 or to any other component of system 100. An alert may comprise one or more of the following types of signals: tactile, vibration, audible, visual, heads-up display or radio frequency signal.

In some instances, a worker may be equipped with multiple different articles of PPE. For instance, a worker may be wearing a PAPR (and headtop) as well as ear-muff style hearing protectors. The ear muff style hearing protectors may include a combination of software and electronics to communicate with other hearing protection or communication devices. The PAPR may also include a combination of hardware and software that provide functionality to operate the PAPR such as modifying blower rate speed, monitoring particulates in the air, or performing any other suitable functions.

In various instances, the worker may wish to determine that PPE worn by the worker is operating correctly (e.g., satisfy one or more self-check criteria). In some examples, self-check criteria may be dynamically based on context data, such as location, environmental characteristics, time, fit with respect to the worker wearing the PPE, or any other type of context data. An article of PPE may include a combination of electronics and software that operates, monitors, and otherwise controls the functionality and operation of the article of PPE. This combination of electronics and software may store data that indicate one or more operating conditions. An operating condition may be assigned one or more states such as OK, warning, failure, and the like. As an example an operating condition for a PAPR may indicate whether the blower is operating according to its designed specification. If the blower is operating when activated by the worker according to its designed specification, the corresponding operating condition may be OK. If the blower is operating when activated by the worker, but outside of its design specification, the corresponding condition may be a warning. If the blower is not operating at all (e.g., blower fan is not rotating) when activated by the worker, the corresponding operating condition may be error. Any number of error states may be possible and any number of operating conditions may be defined for an article of PPE.

Techniques and components of this disclosure provide a self-check procedure that determines whether each article of PPE in a set of PPE (e.g., a set assigned to a worker) are operating correctly. For instance, a data hub worn by a worker may implement a self-check procedure to communicate with one or more other articles of PPE that are communicatively coupled to the data hub and which are assigned to the worker wearing the data hub. The worker may provide a user input at the data hub which initiates the self-check procedure to each other article of PPE. By checking the operating conditions of each article of PPE, the data hub may determine whether a particular article of PPE is or is not operating correctly. In this way, a worker may efficiently and accurately determine if the set of PPE is operating correctly without further technical dissection or evaluation of the PPE, which may not be possible in some environments. Techniques and components are further described with respect to FIG. 1.

Initially, as shown in FIG. 1, a worker may be equipped with clean air supply source 120 and data hub 130. Clean air supply source 120 and headtop 110 may each be communicatively coupled by wireless communication to data hub 130 via communication components respectively included in clean air supply source 120 and headtop 110. As such, data hub 130 may store data that uniquely identifies clean air supply source 120 and headtop 110. Data hub 130 may include a self-check component and self-check data, as further described in FIG. 2. The self-check data may define one or more self-check criteria, which if satisfied or not satisfied, indicate that the articles of PPE are operating correctly. The self-check component may execute a self-check procedure defined by the self-check data to determine the operating conditions of different articles of PPE. For instance, clean air supply source 120 may include a combination of electronics and/or software that indicates an operating condition for the blower as described above, the states being OK, warning, or error. Headtop 110 may also include a sensor that indicate an operating condition for whether the visor is open (e.g., up), closed (e.g., down), or partially opened/closed.

To initiate the self-check, data hub 130 may include a button or other input device 131 through which the user may provide user input to initiate the self-check procedure. Upon detecting the user input at the input device 131, data hub 130 may initiate a broadcast of diagnostic self-check messages to one or more articles of PPE that are communicatively coupled to data hub 130. In some examples, data hub 130 may store a set, list or other structured set of identifiers of articles of PPE that are communicatively coupled to data hub 130. In some examples, data hub 130 mays store data in association with each identifier that indicates whether it may respond to diagnostic self-check messages. Data hub 13 may generate a self-check message for each article of PPE that may respond to self-check messages. In some examples, the message include an identifier of the data hub, an indicator to perform a self-check (or particular type of self-check), a time stamp, or any other information usable to perform the self-check. In some examples, each self-check message contents may be different based on the type of PPE to which the self-check message is destined.

Data hub 130 may upon detecting the user input and identifying each article of PPE, broadest each corresponding message to its corresponding article of PPE. For instance, data hub 130 may send the messages to each communication component of each article of PPE. In some examples, the same self-check message may be sent to each article of PPE. In any case, each article of PPE receives a self-check message at its communication component. In the example of FIG. 1, headtop 110 and clean air supply source 120 may each receive self-check messages. Based on a self-check message, clean air supply source 120 may update and/or select its operating condition states for sending back to data hub 130. For instance, clean air supply 120 may periodically, continuously, or asynchronously (e.g., in response to a self-check message) update its operation condition states.

Clean air supply source 120 may generate a diagnostic acknowledgement message. The diagnostic acknowledgement message may indicate whether the article of PPE is operating correctly. In another example, a diagnostic acknowledgement message may include operating condition states for each operating condition. In some examples, the diagnostic acknowledgement message may include the types or names of the operation conditions. In some examples, the diagnostic acknowledgement message may include a timestamp, identifier of the article of PPE, descriptive data that corresponds to an operating condition, or any other any other information that is associated with the self-check. In the example of FIG. 1, clean air supply source 120 may have a warning state for the blower operating condition described above. As such, clean air supply source 120 may send a diagnostic acknowledgement message that that indicates the warning state for the blower operating condition. Headtop 110 may send a diagnostic acknowledgment message that indicates the visor is down.

Data hub 130 may receive a set of diagnostic acknowledgement messages from headtop 110 and clean air supply source 120 respectively. In response to receiving the diagnostic acknowledgement message, data hub 130 may determine whether these messages satisfy one or more self-check criteria. In some examples, a self-check criterion may correspond to an operating condition. That is, the self-check criterion may determine whether an operating condition state is or is not satisfied. For instance, the self-check criterion may specify a Boolean condition, comparative condition (e.g., greater than, less than, or equal to), or any other type of condition. Data hub 130 may determine whether data in the diagnostic acknowledgement message satisfy one or more self-check criteria. In some instances, a self-check criterion may be comprised of multiple self-check criteria (e.g., each operating condition state in a set of diagnostic acknowledgement messages is OK). In the example of FIG. 1, data hub 130 may include a first self-check criteria for headtop 110 that the visor is down (e.g., not open or partially up/down). Data hub 130 may include a second self-check criteria for clean air supply source 120 that the operating condition state is OK. Data hub 130 may determine, based on the diagnostic acknowledgement messages, that the first self-check criteria is satisfied (e.g., the visor is down), but the second self-check criteria is not satisfied (e.g., the blower operating condition state is warning, i.e., not OK).

Data hub 130 may perform one or more operations based at least in part on whether the one or more self-check criteria are satisfied. For instance, data hub 130 may generate one or more alerts at data hub 130. Alerts may be visual, haptic, audible, or any other mode of output. In some examples, the type or severity (e.g., duration, intensity, etc.) may be based on a type or severity of a self-check criterion being satisfied or not satisfied. In some examples, data hub 130 may send one or more messages to PPEMS 6. The one or more messages may indicate that one or more self-check criteria are not satisfied. In examples, the one or more messages may indicate a worker identifier or other characteristics of a worker, PPE identifier or other characteristics of PPE, work environment identifier or other characteristics of the work environment, timestamp, any information included in the diagnostic acknowledge message or other information received from PPE, worker location, self-check criteria identifier or data about the criteria, or any other data relating to whether the one or more self-check criteria are satisfied. As further described in his disclosure, PPEMS 6 may send alerts to other computing devices, perform analytics based on whether the self-check criteria are satisfied, log self-check information, to name only a few examples.

Although FIG. 1, described the self-check procedure as being performed by data hub 130, such techniques may be performed directly by an article of PPE. For instance, in an alternative example to FIG. 1, the worker may not have a data hub and the self-check procedure may be initiated by clean air supply source 120 which includes the functionality previously described as being included in data hub 130. In this alternative example, clean air supply source 120 may include a combination of electronics and software to perform the self-check procedure including communicatively coupling to other articles of PPE on which the self-check procedure is performed.

Figure 2:
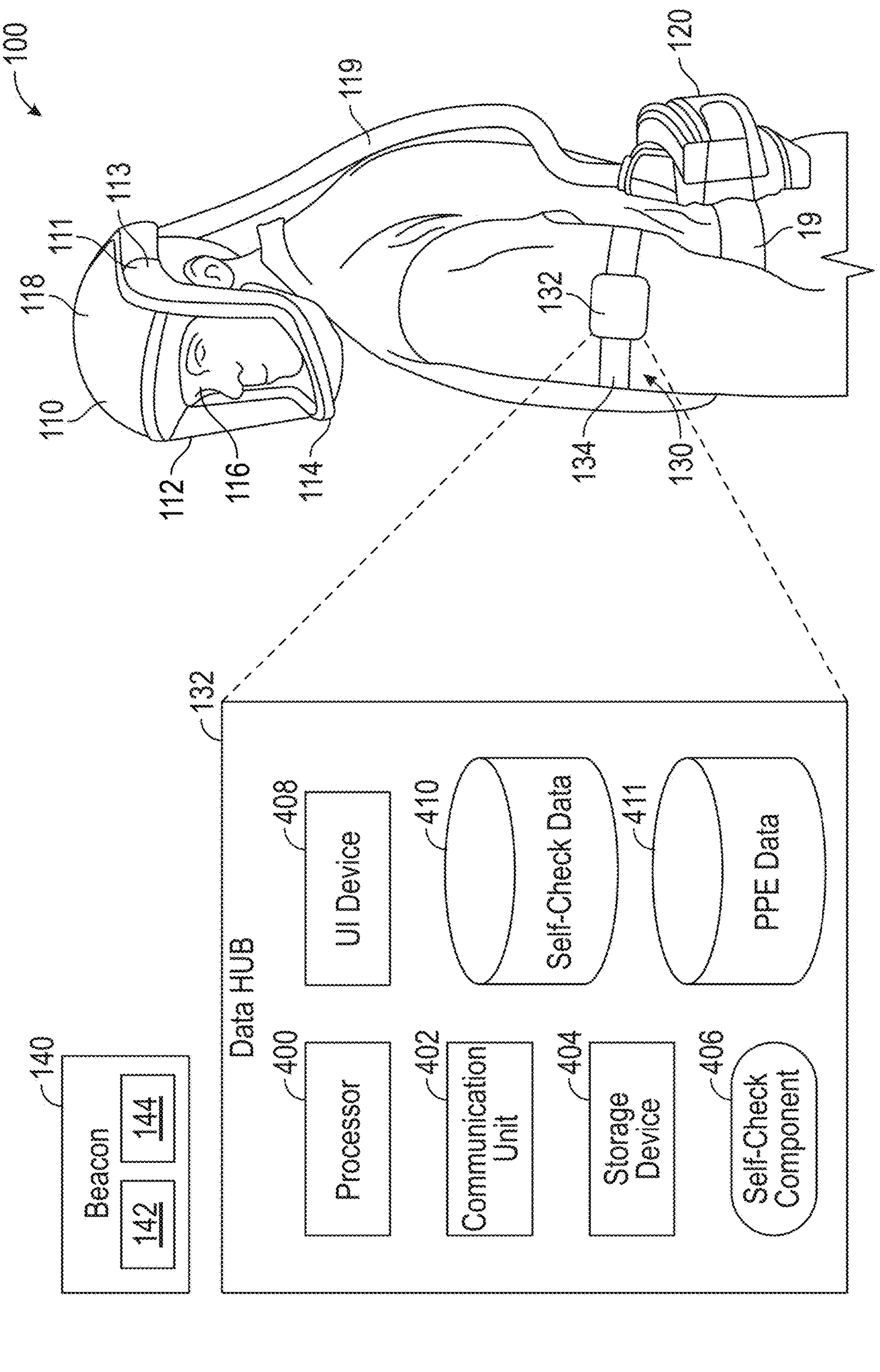
FIG. 2 is a conceptual diagram of a data hub configurable to perform a self-check procedure for one or more articles of PPE, in accordance with one or more techniques of this disclosure.

FIG. 2 is a conceptual diagram of a data hub configurable to perform a self-check procedure for one or more articles of PPE, in accordance with one or more techniques of this disclosure. FIG. 2 illustrates components of data hub 130 including processor 400, communication unit 402, storage device 404, self-check component 406, user-interface device 408, self-check data 410, and PPE data 411. FIG. 2 illustrates only one particular example of data hub 130. Many other examples of data hub 130 may be used in other instances and may include a subset of the components included in example data hub 130 or may include additional components not shown example data hub 130 in FIG. 2. In some examples, data hub 130 may be an intrinsically safe computing device, smartphone, wrist- or head-worn computing device, or any other computing device that may include a set, subset, or superset of functionality or components as shown in data hub 130. Communication channels may interconnect each of the components in data hub 130 for inter-component communications (physically, communicatively, and/or operatively). In some examples, communication channels may include a hardware bus, a network connection, one or more inter-process communication data structures, or any other components for communicating data between hardware and/or software.

One or more processors 400 may implement functionality and/or execute instructions within data hub 130. For example, processor 400 may receive and execute instructions stored by storage devices 404. These instructions executed by processor 400 may cause data hub 130 to store and/or modify information, within storage devices 404 during program execution. Processors 400 may execute instructions of components, such as self-check component 406 to perform one or more operations in accordance with techniques of this disclosure. That is, self-check component 406 may be operable by processor 400 to perform various functions described herein.

Data hub 130 may include one or more user-interface devices 408 to receive user input and/or output information to a user. One or more input components of user-interface devices 408 may receive input. Examples of input are tactile, audio, kinetic, and optical input, to name only a few examples. User-interface devices 408 of data hub 130, in one example, include a mouse, keyboard, voice responsive system, video camera, buttons, control pad, microphone or any other type of device for detecting input from a human or machine. In some examples, UI device 408 may be a presence-sensitive input component, which may include a presence-sensitive screen, touch-sensitive screen, etc.

One or more output components of user-interface devices 408 may generate output. Examples of output are tactile, audio, and video output. Output components of user-interface devices 408, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with data hub 130 in some examples.

UI device 408 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

One or more communication units 402 of data hub 130 may communicate with external devices by transmitting and/or receiving data. For example, data hub 130 may use communication units 402 to transmit and/or receive radio signals on a radio network such as a cellular radio network. In some examples, communication units 402 may transmit and/or receive satellite signals on a satellite network such as a Global Positioning System (GPS) network. Examples of communication units 402 include a network interface card (e.g. such as an Ethernet card), an optical transceiver, a radio frequency transceiver, a GPS receiver, or any other type of device that can send and/or receive information. Other examples of communication units 402 may include Bluetooth®, GPS, 3G, 4G, and Wi-Fi® radios found in mobile devices as well as Universal Serial Bus (USB) controllers and the like.

One or more storage devices 404 within data hub 130 may store information for processing during operation of data hub 130. In some examples, storage device 404 is a temporary memory, meaning that a primary purpose of storage device 404 is not long-term storage. Storage device 404 may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 404, in some examples, also include one or more computer-readable storage media. Storage device 404 may be configured to store larger amounts of information than volatile memory. Storage device 404 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 404 may store program instructions and/or data associated with components such as self-check component 406.

Data hub 130 may also include a power source, such as a battery, to provide power to components shown in data hub 130. A rechargeable battery, such as a Lithium Ion battery, can provide a compact and long-life source of power. Data hub 130 may be adapted to have electrical contacts exposed or accessible from the exterior of the hub to allow recharging the data hub 130.

FIG. 2 illustrates self-check data 410 included in data hub 130 and PPE data 411 included in data hub 130. PPE data 411 may include a list, set, or other structure data identifying each article of PPE that is communicatively coupled to data hub 130. In some examples, PPE data may be unique device identifiers for each of PPE data 411. Data hub 130 may also include self-check data 410. Self-check data 410 may include a set of self-check criteria. In some examples, the self-check criteria may include conditions as described in FIG. 1 that may be tested by self-check component 406. In some examples, self-check data 410 may include a mapping between a self-check criterion and a type of PPE. For instance, a particular self-check criterion that tests for the operating condition of a blower in a clean air supply source may be associated with or mapped to a type indicator for a clean air supply source. In this way, self-check component 406 may apply the corresponding self-check criterion to the corresponding operation condition states or data included in diagnostic acknowledgement messages. In some examples, self-check data 410 may received via communication unit 402 from a computing device, such as PPEMS 6. For instance, PPEMS 6 may receive and/or select information that indicates the set of articles of PPE worn by the worker. PPEMS 6 may send, based on this information, the self-check data to data hub 130 for the worker. As an example, PPEMS 6, may determine that the worker in FIG. 2 includes clean air supply source 120 and headtop 110. Accordingly, PPEMS 6 may select self-check criteria that correspond to the respective types of PPE (e.g., clean air supply source and headtop).

In FIG. 2, data hub 130 may detect a user input UI device 408. Self-check component may, in response to the user input, initiate a broadcast of diagnostic self-check messages to headtop 110 and clean air supply source 120. Self-check component 406 may determine or identify each of headtop 110 and clean air supply source 120 that are identified in PPE data 411 as being communicatively coupled to data hub 130. Self-check component 406 may generate a self-check message for each article of PPE that may respond to self-check messages.

Self-check component 406 may, upon detecting the user input and identifying each article of PPE, cause communication unit 402 to broadcast each corresponding message headtop 110 and clean air supply source 120. For instance, data hub 130 may send the messages to each communication component of headtop 110 and clean air supply source 120. Headtop 110 and clean air supply source 120 may each receive self-check messages. Based on a self-check message, clean air supply source 120 and headtop 110 may update and/or select its operating condition states for sending back to data hub 130.

In FIG. 2, clean air supply source 120 may have a warning state for the blower operating condition described above. As such, clean air supply source 120 may send a diagnostic acknowledgement message that that indicates the warning state for the blower operating condition. Headtop 110 may send a diagnostic acknowledgment message that indicates the visor is down.

Communication unit 402 may receive a set of diagnostic acknowledgement messages from headtop 110 and clean air supply source 120 respectively. In response to receiving the diagnostic acknowledgement message, self-check component 406 may determine whether these messages satisfy one or more self-check criteria included in self-check data 410. In FIG. 2, self-check data 410 may include a first self-check criteria for headtop 110 that the visor is down (e.g., not open or partially up/down). Self-check data 410 may include a second self-check criteria for clean air supply source 120 that the operating condition state is OK. Self-check component 406 may determine, based on the diagnostic acknowledgement messages, that the first self-check criteria is satisfied (e.g., the visor is down), but the second self-check criteria is not satisfied (e.g., the blower operating condition state is warning, i.e., not OK).

Self-check component 406 may perform one or more operations based at least in part on whether the one or more self-check criteria are satisfied. For instance, self-check component 406 may generate one or more alerts using one or more UI devices 408. Self-check component 406 may cause communication unit 402 to send one or more messages to PPEMS 6. The one or more messages may indicate that one or more self-check criteria are not satisfied. In some examples, self-check component 406 may log whether one or more self-check criteria are satisfied in PPE data 411.

In some examples, the input that initiates the self-check at data hub 130 may be an event generated by the data hub in response to at least one of a fall of the particular worker detected by the data hub, a physiological or biometric condition of the particular worker, a characteristic of the work environment, a time, or a location. For instance, if data hub 130 determines that a worker has experienced a fall (e.g., using an accelerometer, model, or any other suitable hardware and/or technique), data hub 130 may initiate a self-check procedure as described in this disclosure to determine the PPE is operating correctly. In another example, if a physiological or biometric condition, such as body temperature, blood pressure, lactic acid, or any other physiological or biometric condition of the user, satisfies a threshold (e.g., greater than, less than, or equal to), then data hub 130 may initiate self-check procedure as described in this disclosure. In some examples, the input that initiates a broadcast of diagnostic self-check messages is received from a remote computing device, such as from PPEMS 6 or a computing device of a user other than the worker (e.g., a safety manager for the worker).

In some examples, data hub 130 and/or PPEMS 6 may determine a correlation between one or more of the set of diagnostic acknowledge messages and one or more other diagnostic acknowledge messages from one or more workers other than the particular worker. In response to determining a correlation, data hub 130 and/or PPEMS 6 may perform one or more operations, such as sending an alert, logging the event, or changing the operation of PPE. As an example, if a worker has manually initiated the self-check procedure repeatedly, such that the number of self-checks exceeds a threshold, data hub 130 and/or PPEMS 6 may perform one or more operations, such as sending an alert, logging the event, or changing the operation of PPE. In some examples, if a worker has manually initiated the self-check procedure repeatedly, such that the number of self-checks corresponds to a number of self-checks of another worker in proximity to the worker (or within a threshold number of self-checks between the two numbers of self-checks by the respective workers), then data hub 130 and/or PPEMS 6 may perform one or more operations, such as sending an alert, logging the event, or changing the operation of PPE.

In some examples, an input at data hub 130 may cause a diagnostic check of at least one of physiological/biometric conditions of the worker and/or of characteristics of the work environment. That is, data hub 130 may perform a self-check of physiological/biometric conditions of the worker for such data that is received or generated by data hub 130 based on physiological/biometric sensors in data hub 130 and/or sensors in PPE communicatively coupled to data hub 130. Data hub 130 may perform a self-check of characteristics of a work environment for such data that is received or generated by data hub 130 based on sensors in data hub 130, sensors in PPE communicatively coupled to data hub 130, and/or sensors in environmental monitoring devices in the work environment. In either case of diagnostic checks for the worker and/or work environment, data hub 130 may, as described in this disclosure with respect to PPE, determine whether one or more self-check criteria for the worker and/or worker environment are satisfied and perform one or more operations based on whether the self-check criteria are satisfied.

Figure 3:
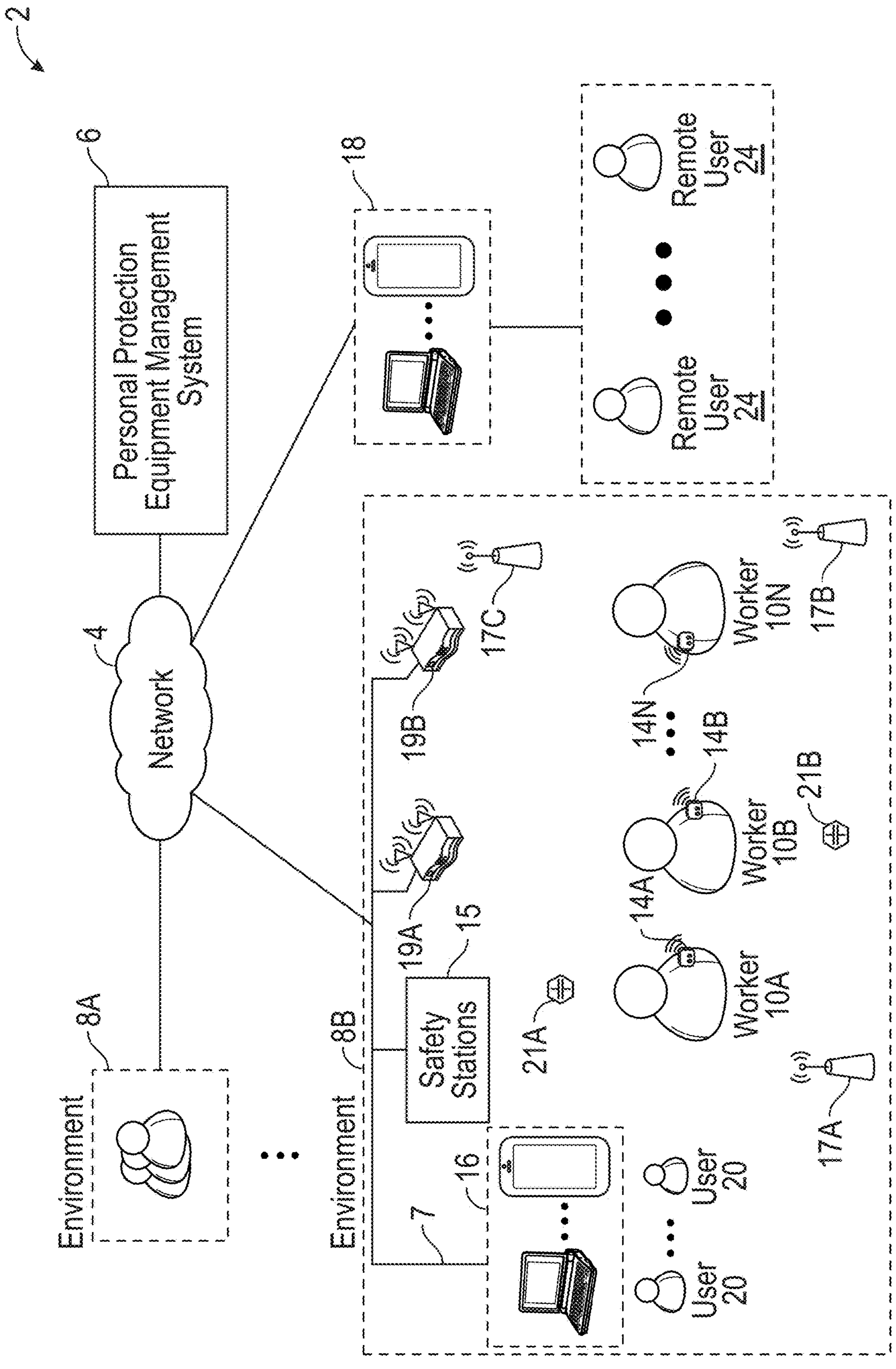
FIG. 3 is a block diagram illustrating an example computing system 2 that includes a personal protection equipment management system (PPEMS) 6 for managing personal protection equipment.

FIG. 3 is a block diagram illustrating an example computing system 2 that includes a personal protection equipment management system (PPEMS) 6 for managing personal protection equipment. As described herein, PPEMS allows authorized users to perform preventive occupational health and safety actions and manage inspections and maintenance of safety protective equipment. By interacting with PPEMS 6, safety professionals can, for example, manage area inspections, worker inspections, worker health and safety compliance training.

In general, PPEMS 6 provides data acquisition, monitoring, activity logging, reporting, predictive analytics, PPE control, and alert generation to name only a few examples. For example, PPEMS 6 includes an underlying analytics and safety event prediction engine and alerting system in accordance with various examples described herein. As further described below, PPEMS 6 provides an integrated suite of personal safety protection equipment management tools and implements various techniques of this disclosure. That is, PPEMS 6 provides an integrated, end-to-end system for managing personal protection equipment, e.g., safety equipment, used by workers 10 within one or more physical environments 8, which may be construction sites, mining or manufacturing sites or any physical environment. The techniques of this disclosure may be realized within various parts of computing environment 2.

As shown in the example of FIG. 3, system 2 represents a computing environment in which a computing device within of a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, utilize personal protection equipment while engaging in tasks or activities within the respective environment.

In this example, environment 8A is shown as generally as having workers 10, while environment 8B is shown in expanded form to provide a more detailed example. In the example of FIG. 1, a plurality of workers 10A-10N may be wearing a variety of different PPE, such as ear muff hearing protectors and a powered-air purifying respirator (PAPR) (further illustrated in FIGS. 1-2).

As further described herein, each of article of PPE may include one or more of embedded sensors, communication components, monitoring devices and processing electronics configured to capture PPE data that corresponds to the PPE in real-time as a user (e.g., worker) engages in activities while wearing the PPE. For example, as described in greater detail with respect to the examples shown in FIGS. 1-2, a PAPR may include a variety of electronic sensors for measuring operations of the PAPR, such as but not limited to: filter type, filter life, air flow rate, and the like. In addition, each article of PPE may include one or more output devices for outputting data that is indicative of operation of the PPE and/or generating and outputting communications to the respective worker 10. For example, articles PPE 11 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In some examples, each of environments 8 include computing facilities (e.g., a local area network) by which articles of PPE assigned to workers 10 are able to communicate with PPEMS 6. For examples, environments 8 may be configured with wireless technology, such as 802.11 wireless networks, 802.15 ZigBee networks, and the like. In the example of FIG. 3, environment 8B includes a local network 7 that provides a packet-based transport medium for communicating with PPEMS 6 via network 4. In addition, environment 8B includes a plurality of wireless access points 19A, 19B that may be geographically distributed throughout the environment to provide support for wireless communications throughout the work environment.

One or more articles of PPE may be configured to communicate data, such as sensed motions, events and conditions, via wireless communications, such as via 802.11 WiFi protocols, Bluetooth protocol or the like. The articles of PPE may, for example, communicate directly with a wireless access point 19. As another example, one or more of workers 10 may be equipped with a respective one of wearable data hubs 14A-14M that enable and facilitate communication between articles of PPE and PPEMS 6. For examples, articles of PPE for a respective worker may communicate with a respective data hub 14 via Bluetooth or other short range protocol, and the data hubs may communicate with PPEMs 6 via wireless communications processed by wireless access points 19. Although shown as wearable devices, hubs 14 may be implemented as standalone devices deployed within environment 8B.

In general, each of hubs 14 operates as a wireless device for articles of PPE relaying communications to and from the PPE, and may be capable of buffering usage data in case communication is lost with PPEMS 6. Moreover, each of hubs 14 is programmable via PPEMS 6 so that local alert rules may be installed and executed without requiring a connection to the cloud. As such, each of hubs 14 provides a relay of streams of usage data from articles of PPE within the respective environment, and provides a local computing environment for localized alerting based on streams of events in the event communication with PPEMS 6 is lost.

As shown in the example of FIG. 3, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Alternatively, beacons 17A-17C may include a pre-programmed identifier that is associated in PPEMS 6 with a particular location. Based on wireless communications with one or more of beacons 17, a given SLR 11 or data hub 14 worn by a worker 10 is configured to determine the location of the worker within work environment 8B. In this way, event data reported to PPEMS 6 may be stamped with positional information to aid analysis, reporting and analytics performed by the PPEMS.

In addition, an environment, such as environment 8B, may also one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional information when reporting environmental data to PPEMS 6. As such, PPEMS 6 may configured to correlate the senses environmental conditions with the particular regions and, therefore, may utilize the captured environmental data when processing event data received from articles of PPE. For example, PPEMS 6 may utilize the environmental data to aid generating alerts or other instructions for articles of PPE and for performing predictive analytics, such as determining any correlations between certain environmental conditions (e.g., heat, humidity, visibility) with abnormal worker behavior or increased safety events. As such, PPEMS 6 may utilize current environmental conditions to aid prediction and avoidance of imminent safety events. Example environmental conditions that may be sensed by sensing devices 21 include but are not limited to temperature, humidity, presence of gas, pressure, visibility, wind and the like.

In example implementations, an environment, such as environment 8B, may also include one or more safety stations 15 distributed throughout the environment to provide viewing stations for accessing PPEMs 6. Safety stations 15 may allow one of workers 10 to check out articles of PPE and/or other safety equipment, verify that safety equipment is appropriate for a particular one of environments 8, and/or exchange data. For example, safety stations 15 may transmit alert rules, software updates, or firmware updates to articles of PPE or other equipment. Safety stations 15 may also receive data cached on articles of PPE, hubs 14, and/or other safety equipment. That is, while articles of PPE (and/or data hubs 14) may typically transmit usage data from sensors of articles of PPE to network 4, in some instances, articles of PPE (and/or data hubs 14) may not have connectivity to network 4. In such instances, articles of PPE (and/or data hubs 14) may store usage data locally and transmit the usage data to safety stations 15 upon being in proximity with safety stations 15. Safety stations 15 may then upload the data from articles of PPE and connect to network 4. In some examples, proximate and/or approaching may mean within a predefined distance, or within a range of wireless communication.

In addition, each of environments 8 include computing facilities that provide an operating environment for end-user computing devices 16 for interacting with PPEMS 6 via network 4. For example, each of environments 8 typically includes one or more safety managers responsible for overseeing safety compliance within the environment. In general, each user 20 interacts with computing devices 16 to access PPEMS 6. Each of environments 8 may include systems. Similarly, remote users may use computing devices 18 to interact with PPEMS via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safely equipment utilized by workers 10, such as accessing and viewing usage records, analytics and reporting. For example, users 20, 24 may review usage information acquired and stored by PPEMS 6, where the usage information may include data specifying starting and ending times over a time duration (e.g., a day, a week, or the like), data collected during particular events, such as detected falls, sensed data acquired from the user, environment data, and the like. In addition, users 20, 24 may interact with PPEMS 6 to perform asset tracking and to schedule maintenance events for individual pieces of safety equipment, e.g., SRLs 11, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

Further, as described herein, PPEMS 6 integrates an event processing platform configured to process thousand or even millions of concurrent streams of events from digitally enabled PPEs. An underlying analytics engine of PPEMS 6 applies historical data and models to the inbound streams to compute assertions, such as identified anomalies or predicted occurrences of safety events based on conditions or behavior patterns of workers 10. Further, PPEMS 6 provides real-time alerting and reporting to notify workers 10 and/or users 20, 24 of any predicted events, anomalies, trends, and the like.

The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protection equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety information, compliance information and any results of the analytic engine, e.g., by the way of dashboards, alert notifications, reports and the like. That is, users 24, 26, or software executing on computing devices 16, 18, may submit queries to PPEMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 2 exhibiting anomalous occurrences of safety events relative to other environments, and the like.

As illustrated in detail below, PPEMS 6 may simplify workflows for individuals charged with monitoring and ensure safety compliance for an entity or environment. That is, the techniques of this disclosure may enable active safety management and allow an organization to take preventative or correction actions with respect to certain regions within environments 8, particular pieces of safety equipment 11 or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment. In this manner, PPEMS 6 may identify individual pieces of PPE or workers 10 for which the metrics do not meet the benchmarks and prompt the users to intervene and/or perform procedures to improve the metrics relative to the benchmarks, thereby ensuring compliance and actively managing safety for workers 10.

In the example of FIG. 3, data hub 14A receives self-check data from PPEMS 6 via network 4. For instance, PPEMS 6 may receive and/or select information that indicates the set of articles of PPE worn by the worker. PPEMS 6 may send, based on this information, the self-check data to data hub 14A for worker 10A. In FIG. 3, PPEMS 6 determines that worker 10A is equipped with clean air supply source 120 and headtop 110. Accordingly, PPEMS 6 may select self-check criteria that correspond to the respective types of PPE (e.g., clean air supply source and headtop).

Data hub 14A may detect a user input, such as a user pressing a button to initiate a self-check. Data hub 14A may, in response to the user input, initiate a broadcast of diagnostic self-check messages to a headtop and clean air supply source worn by user 10A. Data hub 14A may determine or identify each of the headtop and clean air supply source that are identified in data hub 14A as being communicatively coupled to data hub 14A. Data hub 14A may generate a self-check message for each article of PPE that may respond to self-check messages.

Data hub 14A may, upon detecting the user input and identifying each article of PPE, broadcast each corresponding message to the headtop and clean air supply source. The headtop and clean air supply source may each receive self-check messages. Based on a self-check message, the clean air supply source and headtop may update and/or select its operating condition states for sending back to data hub 14A.

As described in FIGS. 1 and 2, the clean air supply source may have a warning state for the blower operating condition. As such, the clean air supply source may send a diagnostic acknowledgement message that that indicates the warning state for the blower operating condition. The headtop may send a diagnostic acknowledgment message that indicates the visor is down.

Data hub 14A may receive a set of diagnostic acknowledgement messages from the headtop and clean air supply source respectively. In response to receiving the diagnostic acknowledgement message, data hub 14A may determine whether these messages satisfy one or more self-check criteria. Data hub 14A may determine, based on the diagnostic acknowledgement messages, that a first self-check criteria is satisfied (e.g., the visor is down), but a second self-check criteria is not satisfied (e.g., the blower operating condition state is warning, i.e., not OK).

Data hub 14A may perform one or more operations based at least in part on whether the one or more self-check criteria are satisfied. For instance, data hub 14A may generate one or more alerts using at data hub 14A. Data hub 14A may send one or more messages to PPEMS 6. The one or more messages may indicate that one or more self-check criteria are not satisfied. In some examples, data hub 14A may log whether one or more self-check criteria are satisfied, and/or in some examples send such logged data to PPEMS 6 for logging for further processing.

Figure 4:
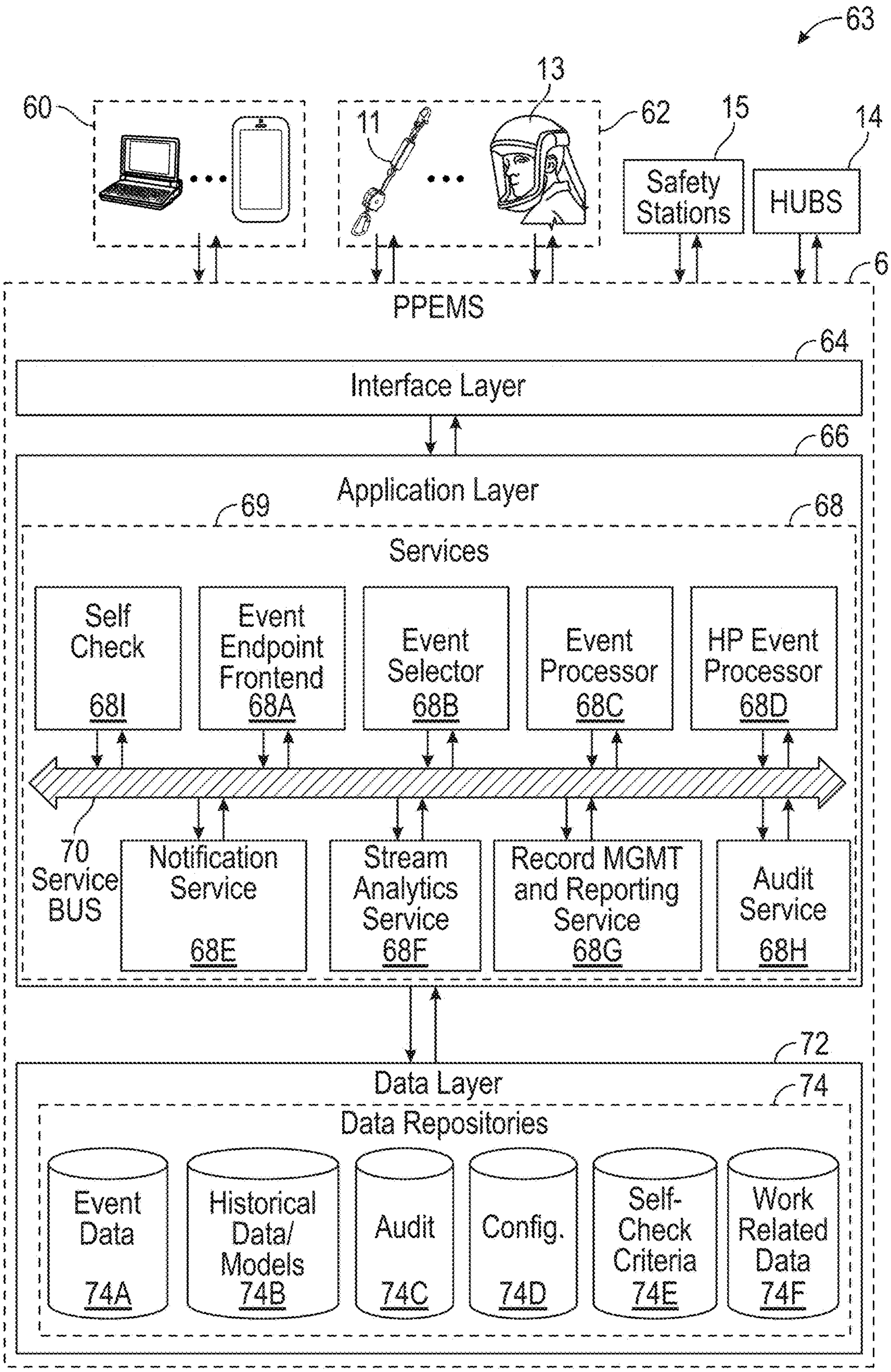
FIG. 4 is a block diagram providing an operating perspective of PPEMS 6, in accordance with one or more techniques of this disclosure.

FIG. 4 is a block diagram providing an operating perspective of PPEMS 6 when hosted as cloud-based platform capable of supporting multiple, distinct work environments 8 having an overall population of workers 10 having a variety of communication enabled personal protection equipment (PPES), such as safety release lines (SRLs) 11, respirators 13, safety helmets or other safety equipment. In the example of FIG. 4, the components of PPEMS 6 are arranged according to multiple logical layers that implement the techniques of the disclosure. Each layer may be implemented by a one or more modules comprised of hardware, software, or a combination of hardware and software.

In FIG. 4, personal protection equipment (PPEs) 62, such as SRLs 11, respirators 13 and/or other equipment, either directly or by way of hubs 14, as well as computing devices 60, operate as clients 63 that communicate with PPEMS 6 via interface layer 64. Computing devices 60 typically execute client software applications, such as desktop applications, mobile application, and web applications. Computing devices 60 may represent any of computing devices 16, 18 of FIG. 1. Examples of computing devices 60 may include, but are not limited to: a portable or mobile computing device (e.g., smartphone, wearable computing device, tablet), laptop computers, desktop computers, smart television platforms, and servers, to name only a few examples.

As further described in this disclosure, PPEs 62 communicate with PPEMS 6 (directly or via hubs 14) to provide streams of data acquired from embedded sensors and other monitoring circuitry and receive from PPEMS 6 alerts, configuration and other communications. Client applications executing on computing devices 60 may communicate with PPEMS 6 to send and receive information that is retrieved, stored, generated, and/or otherwise processed by services 68. For instance, the client applications may request and edit safety event information including analytical data stored at and/or managed by PPEMS 6. In some examples, client applications 61 may request and display aggregate safety event information that summarizes or otherwise aggregates numerous individual instances of safety events and corresponding data acquired from PEPs 62 and or generated by PPEMS 6. The client applications may interact with PPEMS 6 to query for analytics information about past and predicted safety events, behavior trends of workers 10, to name only a few examples. In some examples, the client applications may output for display information received from PPEMS 6 to visualize such information for users of clients 63. As further illustrated and described in below, PPEMS 6 may provide information to the client applications, which the client applications output for display in user interfaces.

Clients applications executing on computing devices 60 may be implemented for different platforms but include similar or the same functionality. For instance, a client application may be a desktop application compiled to run on a desktop operating system, such as Microsoft Windows, Apple OS X, or Linux, to name only a few examples. As another example, client application 61 may be a mobile application compiled to run on a mobile operating system, such as Google Android, Apple IOS, Microsoft Windows Mobile, or BlackBerry OS to name only a few examples. As another example, a client applications may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 4, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward information from the requests to services 68, and provide one or more responses, based on information received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the information to application layer 66, which includes services 68.

As shown in FIG. 4, PPEMS 6 also includes an application layer 66 that represents a collection of services for implementing much of the underlying operations of PPEMS 6. Application layer 66 receives information included in requests received from client applications 61 and further processes the information according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents a logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate information to one another. As another example, services 68 may communicate in point-to-point fashion using sockets or other communication mechanism. In still other examples, a pipeline system architecture could be used to enforce a workflow and logical processing of data a messages as they are process by the software system services. Before describing the functionality of each of services 68, the layers is briefly described herein.

Data layer 72 of PPEMS 6 represents a data repository that provides persistence for information in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage information in data repositories 74. The RDBMS software may manage one or more data repositories 74, which may be accessed using Structured Query Language (SQL). Information in the one or more databases may be stored, retrieved, and modified using the RDBMS software. In some examples, data layer 72 may be implemented using an Object Database Management System (ODBMS), Online Analytical Processing (OLAP) database or other suitable data management system. Data repositories 74 are further described herein.

As shown in FIG. 2, each of services 68A-68H ("services 68") are implemented in a modular form within PPEMS 6. Although shown as separately modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors.

In some examples, one or more of services 68 may each provide one or more interfaces that are exposed through interface layer 64. Accordingly, client applications 61 may call one or more interfaces of one or more of services 68 to perform techniques of this disclosure.

In accordance with techniques of the disclosure, services 68 may include an event processing platform including an event endpoint frontend 68A, event selector 68B, event processor 68C and high priority (HP) event processor 68D. Event endpoint frontend 68A operates as a front end interface for receiving and sending communications to PPEs 62 and hubs 14. In other words, event endpoint frontend 68A may operate as a front line interface to safety equipment deployed within environments 8 and utilized by workers 10. In some instances, event endpoint frontend 68A may receive numerous event streams 69 of communications from the PPEs 62 carrying data sensed and captured by the safety equipment. Each incoming communication may, for example, carry data recently capture representing sensed conditions, motions, temperatures, actions or other data, generally referred to as events. Communications exchanged between the event endpoint frontend 68A and the PPEs may be real-time or pseudo real-time depending on communication delays and continuity.

Event selector 68B operates on the stream of events 69 received from PPEs 62 and/or hubs 14 via frontend 68A and determines, based on rules or classifications, priorities associated with the incoming events. Based on the priorities, event selector 68B enqueues the events for subsequent processing by event processor 68C or high priority (HP) event processor 68D.

In general, event processor 68C or high priority (HP) event processor 68D operate on the incoming streams of events to update event data 74A within data repositories 74. For instance, event processors 68C, 68D may create, read, update, and delete event information stored in event data 74A. Event information for may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 68B directs the incoming stream of events to stream analytics service 68F, which is configured to process the incoming stream of events to perform real-time analytics. Stream analytics service 68F may, for example, be configured to process and compare multiple streams of event data with historical values and models 74B in real-time as event data is received. In this way, stream analytic service 68D may be configured to detect anomalies, transform incoming event data values, trigger alerts upon detecting safety concerns based on conditions or worker behaviors. Historical values and models 74B may include, for example, specified safety rules, business rules and the like. In addition, stream analytic service 68D may generate output for communicating to PPPEs 62 by notification service 68F or computing devices 60 by way of record management and reporting service 68D.

Analytics service 68F processes inbound streams of events, potentially hundreds or thousands of streams of events, from enabled safety PEP 62 utilized by workers 10 within environments 8 to apply historical data and models 74B to compute assertions, such as identified anomalies or predicted occurrences of imminent safety events based on conditions or behavior patterns of the workers. Analytics service 68D may publish the assertions to notification service 68F and/or record management by service bus 70 for output to any of clients 63. In this way, analytics service 68F may configured as an active safety management system that predicts imminent safety concerns and provides real-time alerting and reporting. In addition, analytics service 68F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 68F may apply historical data and models 74B to determine for a particular work, the likelihood that a safety event is imminent for the worker based on detected behavior or activity patterns, environmental conditions and geographic locations. In some examples, analytics service 68F may determine whether a worker is currently impaired, e.g., due to possible alcohol or drugs, and may require intervention to prevent safety events. As yet another example, analytics service 68F may provide comparative ratings of workers or type of safety equipment in a particular environment 8.

Analytics service 68F may maintain or otherwise use one or more models that provide risk metrics to predict patient outcomes. Analytics service 68F may also generate order sets, recommendations, and quality measures. In some examples, analytics service 68F may generate user interfaces based on processing information stored by PPEMS 6 to provide actionable information to any of clients 63.

Although other technologies can be used, in one example implementation, analytics service 68F utilizes machine learning when operating on streams of safety events so as to perform real-time analytics. That is, analytics service 68F includes executable code generated by application of machine learning to training data of event streams and known safety events to detect patterns. The executable code may take the form of software instructions or rule sets and is generally referred to as a model that can subsequently be applied to event streams 69 for detecting similar patterns and predicting upcoming events. Alternatively, or in addition, analytics may communicate all or portions of the generated code and/or the machine learning models to hubs 16 for execution thereon so as to provide local alerting in near-real time to PPEs. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups/types of PPEs 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the patient information over the period of time.

In example implementations, services 68 may also include security service 68E that authenticate and authorize users and requests with PPEMS 6. Specifically, security service 68E may receive authentication requests from client applications and/or other services 68 to access data in data layer 72 and/or perform processing in application layer 66. An authentication request may include credentials, such as a username and password. Security service 68E may query security data 74A to determine whether the username and password combination is valid. Configuration data 74D may include security data in the form of authorization credentials, policies, and any other information for controlling access to PPEMS 6. As described above, security data 74A may include authorization credentials, such as combinations of valid usernames and passwords for authorized users of PPEMS 6. Other credentials may include device identifiers or device profiles that are allowed to access PPEMS 6.

Services 68 may also include an audit service 68I that provides audit and logging functionality for operations performed at PPEMS 6. For instance, audit services 68I may log operations performed by services 68 and/or data accessed by services 68 in data layer 72. Audit services 68I may store audit information such as logged operations, accessed data, and rule processing results in audit data 74C. In some examples, audit service 68I may generate events in response to one or more rules being satisfied. Audit service 68I may store data indicating the events in audit data 74C.

PPEMS 6 may include self-check component 68I, self-check criteria 74E and work relation data 74F. Self-check criteria 74E may include one or more self-check criterion as described in this disclosure. Work relation data 74F may include mappings between data that corresponds to PPE, workers, and work environments. Work relation data 74F may be any suitable datastore for storing, retrieving, updating and deleting data. RMRS 69G may store a mapping between the unique identifier of worker 10A and a unique device identifier of data hub 14A. Work relation data store 74F may also map a worker to an environment. In the example of FIG. 4, self-check component 68I may receive or otherwise determine data from work relation data 74F for data hub 14A, worker 10A, and/or PPE associated with or assigned to worker 10A. Based on this data, self-check component 68I may select one or more self-check criteria from self-check criteria 74E. Self-check component 68I may send the self-check criteria to data hub 14A.

As described in FIGS. 1-2, a data hub may send messages that indicate whether one or more self-check criteria have been satisfied. Interface layer 64 may receive the messages and self-check component 68I may store data from the messages in work relation data 74F. in some examples, if self-check component 68I determines that the message satisfies and alert criterion (e.g., which may be configured by any user of PPEMS 6), self-check 68I may cause notification service 68E to send a notification to one or more recipient computing devices. For instance, if self-check 68I receives a message that indicates a self-check criteria has failed, self-check component 68I may cause notification service 68E to send a message to a safety manager for the worker for which the self-check procedure failed.

In some examples, stream analytics service 68F may process a message that indicates whether one or more self-check criteria have been satisfied in a set of other past messages stored in historical data models 74B. In other examples, stream analytics service 68F may process a message that indicates whether one or more self-check criteria have been satisfied in a stream of similar message. In either case, stream analytics service 68F may detect an anomaly and cause notification service 68E to send a notification to one or more computing devices (e.g., of a safety manager, worker, and/or other workers near the worker for which the self-check failed).

Figure 5:
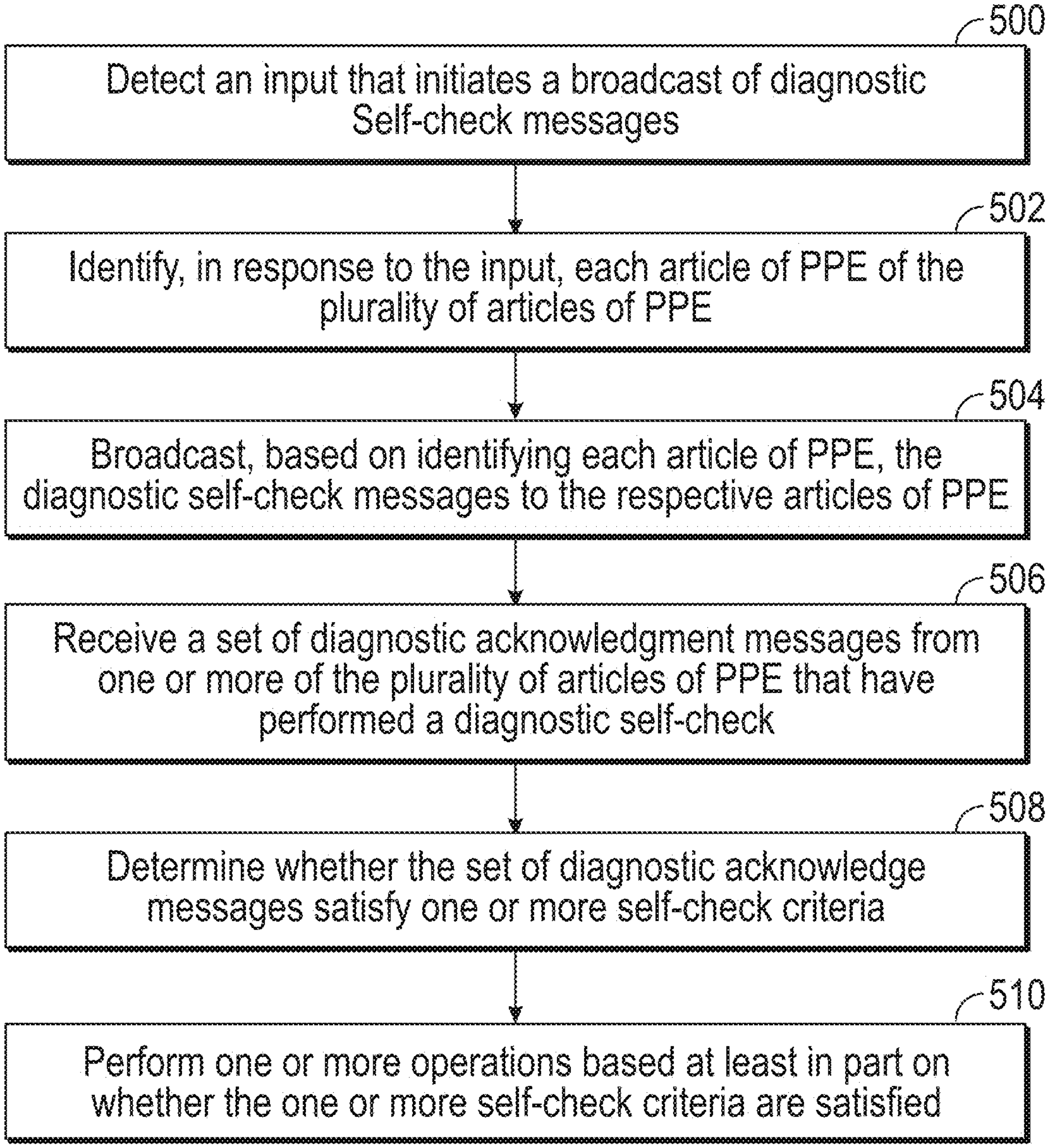
FIG. 5 is a flow diagram illustrating example operations to perform a PPE self-check procedure, in accordance with techniques of this disclosure.

FIG. 5 is a flow diagram illustrating example operations to perform a PPE self-check procedure, in accordance with techniques of this disclosure. For purposes of illustration only, the example operations are described below within the context of a computing device, such as data hub 130, as described in this disclosure. The computing device may detect an input that initiates a broadcast of diagnostic self-check messages (500). In response to input, the computing device may identify each article of PPE of a plurality of articles of PPE that are communicatively coupled to the computing device (502). The computing device may broadcast, based on identifying each article of PPE, the diagnostic self-check messages to the respective articles of PPE (504). Each article of PPE receives its respective self-check message at its communication component. The computing device may receive a set of diagnostic acknowledgement messages from one or more of the plurality of articles of PPE that have performed a diagnostic self-check (506). The computing device may determine whether the set of diagnostic acknowledge messages satisfy one or more self-check criteria (508). In the example of FIG. 5, the computing device may perform one or more operations based at least in part on whether the one or more self-check criteria are satisfied (510).

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out all together (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. A system comprising:

at least a first respirator and second respirator, each comprising a communication component, and each the first and second respirators worn by a particular worker; and a data hub comprising a communication unit, one or more computer processors, and a memory comprising instructions that when executed by the one or more computer processors cause the one or more computer processors to:

receive, via the communication unit, at least one first diagnostic acknowledgement message from the first respirator that the first respirator has performed a first diagnostic self-check, wherein the first diagnostic acknowledgment message at least includes an identifier of the first respirator and data indicative of a respective state of the first respirator;

receive, via the communication unit, at least one second diagnostic acknowledgement message from the second respirator that has performed a second diagnostic self-check, where the second diagnostic acknowledgement message at least includes an identifier of the second respirator and data indicative of a respective state of the second respirator;

determine whether the first and second acknowledgement messages together satisfy one or more self-check criteria corresponding to proper operation of the first and second respirators; and perform one or more operations based at least in part on whether the one or more self-check criteria are satisfied.

2. The system of claim 1, wherein the instructions that cause the one or more computer processors to perform the one or more operations based at least in part on whether the one or more self-check criteria are satisfied comprise instructions that when executed by the one or more computer processors cause the one or more computer processors to generate an alert at the data hub, wherein the alert is at least one of an audible, a haptic, or a visual alert.

3. The system of claim 1, wherein to perform the one or more operations based at least in part on whether the one or more self-check criteria are satisfied, the memory of the data hub comprises the instructions that when executed by the one or more computer processors cause the one or more computer processors to initiate, via the communication unit, sending of a message to a remote computing device that indicates whether the first and second diagnostic acknowledgement messages satisfy the one or more self-check criteria.

4. The system of claim 1, further comprising a remote computing device, wherein the remote computing device, in response to receiving a message that indicates whether the diagnostic acknowledgement messages from the first and second respirators together satisfy the one or more self-check criteria, sends an indication to a computing device of a safety manager of a particular worker that indicates whether the first and second diagnostic acknowledgement messages satisfy one or more self-check criteria.

5. The system of claim 1, further comprising a remote computing device, wherein the remote computing device determines an anomaly based at least in part on a message from the data hub and at least one previously received message that indicates whether the first and second diagnostic acknowledgement messages together satisfy the one or more self-check criteria, and wherein the indication sent to a computing device of a safety manager of the particular worker is sent in response to the determining of the anomaly.

6. The system of claim 1, wherein the memory of the data hub further comprises instructions that, when executed by the one or more computer processors, cause the one or more computer processors to determine a correlation between the first and second diagnostic acknowledgement messages and one or more other diagnostic acknowledge messages associated with one or more workers other than the particular worker.

7. The system of claim 1, further comprising a remote computing device, wherein the remote computing device, in response to receiving the first and second diagnostic acknowledgement messages, sends a message to the data hub that causes a change in an operation of at least one of the first respirator or the second respirator.

8. A computing device comprising:

a communication unit;

one or more computer processors; and a memory comprising instructions that when executed by the one or more computer processors cause the one or more computer processors to:

receive, via the communication unit, at least one first diagnostic acknowledgement message from a first respirator that has performed a respective first diagnostic self-check, wherein the diagnostic acknowledgement message at least includes an identifier of the first respirator and data indicative of a respective state of the first respirator, wherein the first respirator is worn by a particular worker;

receive, via the communication unit, at least one second diagnostic acknowledgement message from a second respirator that has performed a respective diagnostic self-check, wherein the diagnostic acknowledgement message at least includes an identifier of the second respirator and data indicative of a respective state of the second respirator, wherein the second respirator is worn by the particular worker;

determine whether the first and second diagnostic acknowledgement messages received from the first and second respirators together satisfy one or more self-check criteria; and perform one or more operations based at least in part on whether the one or more self-check criteria are satisfied.

9. The computing device of claim 8, wherein the instructions that cause the one or more computer processors to perform the one or more operations based at least in part on whether the one or more self-check criteria are satisfied comprise instructions that when executed by the one or more computer processors cause the one or more computer processors to generate an alert at a data hub, wherein the alert is at least one of an audible, a haptic, or a visual alert.

10. The computing device claim 8, wherein the instructions that cause the one or more computer processors to perform the one or more operations based at least in part on whether the one or more self-check criteria are satisfied comprise instructions that when executed by the one or more computer processors cause the one or more computer processors to initiate, via the communication unit, sending of a message to a remote computing device that indicates whether the first and second diagnostic acknowledgement messages satisfy the one or more self-check criteria.

11. The computing device of claim 8, wherein the memory further comprises instructions that when executed by the one or more computer processors cause the one or more computer processors to, in response to receiving the message that indicates whether the first and second diagnostic acknowledgment messages together satisfy the one or more self-check criteria, send an indication to a computing device of a safety manager of the particular worker, the message indicating whether the first and second diagnostic acknowledgment messages satisfy one or more self-check criteria.

12. The computing device of claim 8, wherein a remote computing device determines an anomaly based at least in part the message from the data hub and at least one previously received message that indicates whether the first and second diagnostic acknowledgment messages together satisfy the one or more self-check criteria, and wherein the indication sent to a computing device of a safety manager of the particular worker is sent in response to the determining of the anomaly.

13. A method comprising:

receiving, via a communication unit, at least one first diagnostic acknowledgment message and at least one second diagnostic acknowledgment message from a set of respirators worn by a particular worker, wherein each respective respirator of the set of respirators has performed a respective diagnostic self-check, wherein each respective diagnostic acknowledgment message at least includes an identifier of the respective respirator and data indicative of a respective state of the respective respirator;

determining that the respective diagnostic acknowledgement messages together satisfy one or more self-check criteria; and performing one or more operations based at least in part on the determination that the one or more self-check criteria are satisfied.

14. The method of claim 13, further comprising:

generating, based at least in part on determining that the respective diagnostic acknowledgement messages together satisfy the one or more self-check criteria, an alert at a computing device, wherein the alert is at least one of an audible, a haptic, or a visual alert.

15. The method of claim 13, further comprising:

initiating, via the communication unit and based at least in part on determining that the first and second diagnostic acknowledgment messages together satisfy the one or more self-check criteria, sending a message to a remote computing device, the sent message indicating whether the first and second diagnostic acknowledgment messages together satisfy the one or more self-check criteria.

* * * * *